(12) United States Patent
Chui et al.

(10) Patent No.: US 11,399,790 B2
(45) Date of Patent: Aug. 2, 2022

(54) SYSTEM AND METHOD FOR HIERARCHICAL MULTI-LEVEL FEATURE IMAGE SYNTHESIS AND REPRESENTATION

(71) Applicant: HOLOGIC, INC., Marlborough, MA (US)

(72) Inventors: Haili Chui, Fremont, CA (US); Liyang Wei, San Jose, CA (US); Jun Ge, Cupertino, CA (US); Xiangwei Zhang, Fremont, CA (US); Nikolaos Gkanatsios, Danbury, CT (US)

(73) Assignee: Hologic, Inc., Marlborough, MA (US)

( * ) Notice: Subject to any disclaimer, the term of this patent is extended or adjusted under 35 U.S.C. 154(b) by 0 days.

(21) Appl. No.: 16/497,764

(22) PCT Filed: Mar. 28, 2018

(86) PCT No.: PCT/US2018/024911
§ 371 (c)(1),
(2) Date: Sep. 25, 2019

(87) PCT Pub. No.: WO2018/183548
PCT Pub. Date: Oct. 4, 2018

(65) Prior Publication Data
US 2021/0113167 A1  Apr. 22, 2021

Related U.S. Application Data

(60) Provisional application No. 62/478,977, filed on Mar. 30, 2017.

(51) Int. Cl.
*G06K 9/00* (2006.01)
*A61B 6/00* (2006.01)
(Continued)

(52) U.S. Cl.
CPC .............. *A61B 6/502* (2013.01); *A61B 6/025* (2013.01); *G06K 9/6292* (2013.01);
(Continued)

(58) Field of Classification Search
USPC ....... 382/100, 103, 128–134, 154, 162, 173, 382/181, 190, 199, 224, 254, 275–276,
(Continued)

(56) References Cited

U.S. PATENT DOCUMENTS

| 7,218,766 B2 | 5/2007 | Eberhard |
| 7,577,282 B2 | 8/2009 | Gkanatsios et al. |

(Continued)

FOREIGN PATENT DOCUMENTS

| AU | 2014339982 | 5/2016 |
| WO | WO 2013123091 | 8/2013 |

(Continued)

OTHER PUBLICATIONS

Non-Final Office Action for U.S. Appl. No. 16/497,766 dated Feb. 3, 2021.
(Continued)

*Primary Examiner* — Seyed H Azarian
(74) *Attorney, Agent, or Firm* — Merchant & Gould P.C.

(57) ABSTRACT

A method for processing breast tissue image data includes processing the image data to generate a set of image slices collectively depicting the patient's breast; for each image slice, applying one or more filters associated with a plurality of multi-level feature modules, each configured to represent and recognize an assigned characteristic or feature of a high-dimensional object; generating at each multi-level feature module a feature map depicting regions of the image slice having the assigned feature; combining the feature maps generated from the plurality of multi-level feature modules into a combined image object map indicating a (Continued)

probability that the high-dimensional object is present at a particular location of the image slice; and creating a 2D synthesized image identifying one or more high-dimensional objects based at least in part on object maps generated for a plurality of image slices.

17 Claims, 9 Drawing Sheets

(51) Int. Cl.
```
A61B 6/02      (2006.01)
G06K 9/62      (2022.01)
G06T 7/00      (2017.01)
G06T 17/10     (2006.01)
```
(52) U.S. Cl.
CPC .......... *G06T 7/0012* (2013.01); *G06T 17/10* (2013.01); *G06T 2207/30068* (2013.01)

(58) Field of Classification Search
USPC ..... 382/285–291, 305, 260; 715/771; 378/4, 378/21
See application file for complete search history.

(56) References Cited

U.S. PATENT DOCUMENTS

| | | | |
|---|---|---|---|
| 7,606,801 B2* | 10/2009 | Faitelson | G06Q 20/382 705/64 |
| 7,702,142 B2* | 4/2010 | Ren | G06T 7/30 378/68 |
| 7,760,924 B2* | 7/2010 | Ruth | G06T 11/006 382/128 |
| 8,571,289 B2 | 10/2013 | Ruth et al. | |
| 2006/0210131 A1 | 9/2006 | Wheeler | |
| 2010/0166267 A1 | 7/2010 | Zhang et al. | |
| 2011/0110576 A1 | 5/2011 | Kreeger et al. | |
| 2012/0014578 A1 | 1/2012 | Karssemeijer et al. | |
| 2013/0059758 A1 | 3/2013 | Haick et al. | |
| 2014/0219548 A1 | 8/2014 | Wels | |
| 2015/0052471 A1* | 2/2015 | Chen | G06T 7/0012 715/771 |
| 2015/0061582 A1 | 4/2015 | Smith | |
| 2016/0051215 A1 | 2/2016 | Chen et al. | |
| 2016/0078645 A1 | 3/2016 | Abdurahman | |
| 2016/0228034 A1* | 8/2016 | Gluncic | A61B 6/12 |
| 2016/0235380 A1 | 8/2016 | Smith et al. | |
| 2016/0367210 A1* | 12/2016 | Gkanatsios | A61B 6/5223 |
| 2017/0071562 A1 | 3/2017 | Suzuki | |
| 2021/0100518 A1 | 4/2021 | Chui | |
| 2021/0118199 A1 | 4/2021 | Chui | |

FOREIGN PATENT DOCUMENTS

| | | |
|---|---|---|
| WO | WO 2014207080 | 12/2014 |
| WO | 2015/061582 | 4/2015 |
| WO | 2018/183549 | 10/2018 |
| WO | 2018/183550 | 10/2018 |
| WO | WO2018/183548 | 10/2018 |

OTHER PUBLICATIONS

M. Ertas, A. Akan, I. Yildirim, A. Dinlerand M. Kamasak, "2D versus 3D total variation minimization in digital breast tomosynthesis," 2015 IEEE International Conference on Imaging Systems and Techniques (1st), Macau, 2015, pp. 1-4, doi: 10.1109/IST.2015. 7294553. (Year: 2015).

B. E. Caroline and N. Vaijayanthi, "Computer aided detection of masses in digital breast tomosynthesis: A review," 2012 International Conference on Emerging Trends in Science, Engineering and Technology (INCOSET), Tiruchirappalli, 2012, pp. 186-191, doi: 10.1109/1 NCOSET.2012.6513903 (Year: 2012).

Non-Final Office Action for U.S. Appl. No. 16/497,767 dated Feb. 19, 2021.

International Search Report and Written Opinion dated Jul. 2, 2018 for PCT application No. PCT/US2018/024911, applicant Hologic, Inc., 10 pages.

PCT International Preliminary Reporton Patentability in International Application PCT/US2018/024911, dated Oct. 10, 2019, 8 pages.

\* cited by examiner

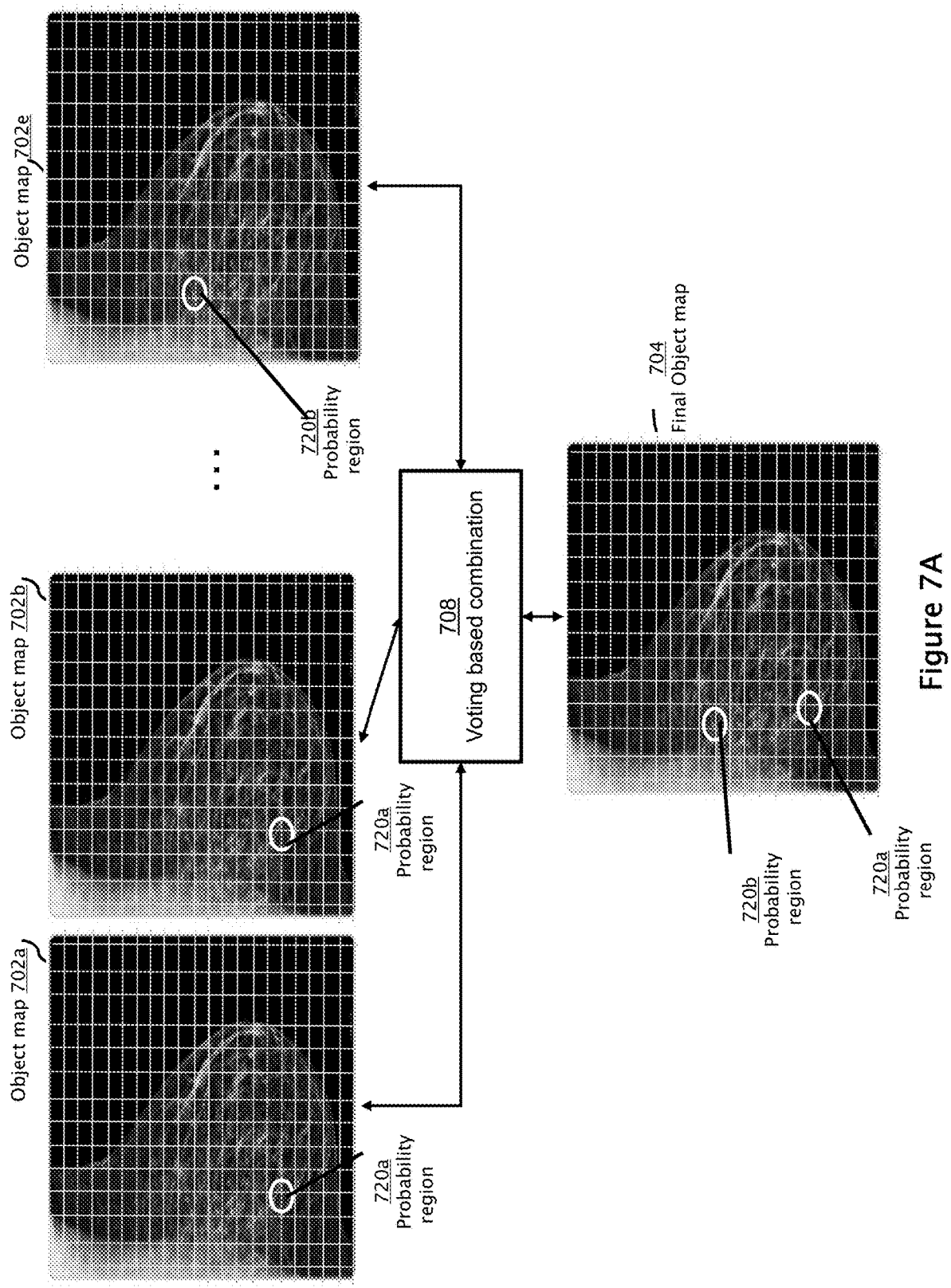

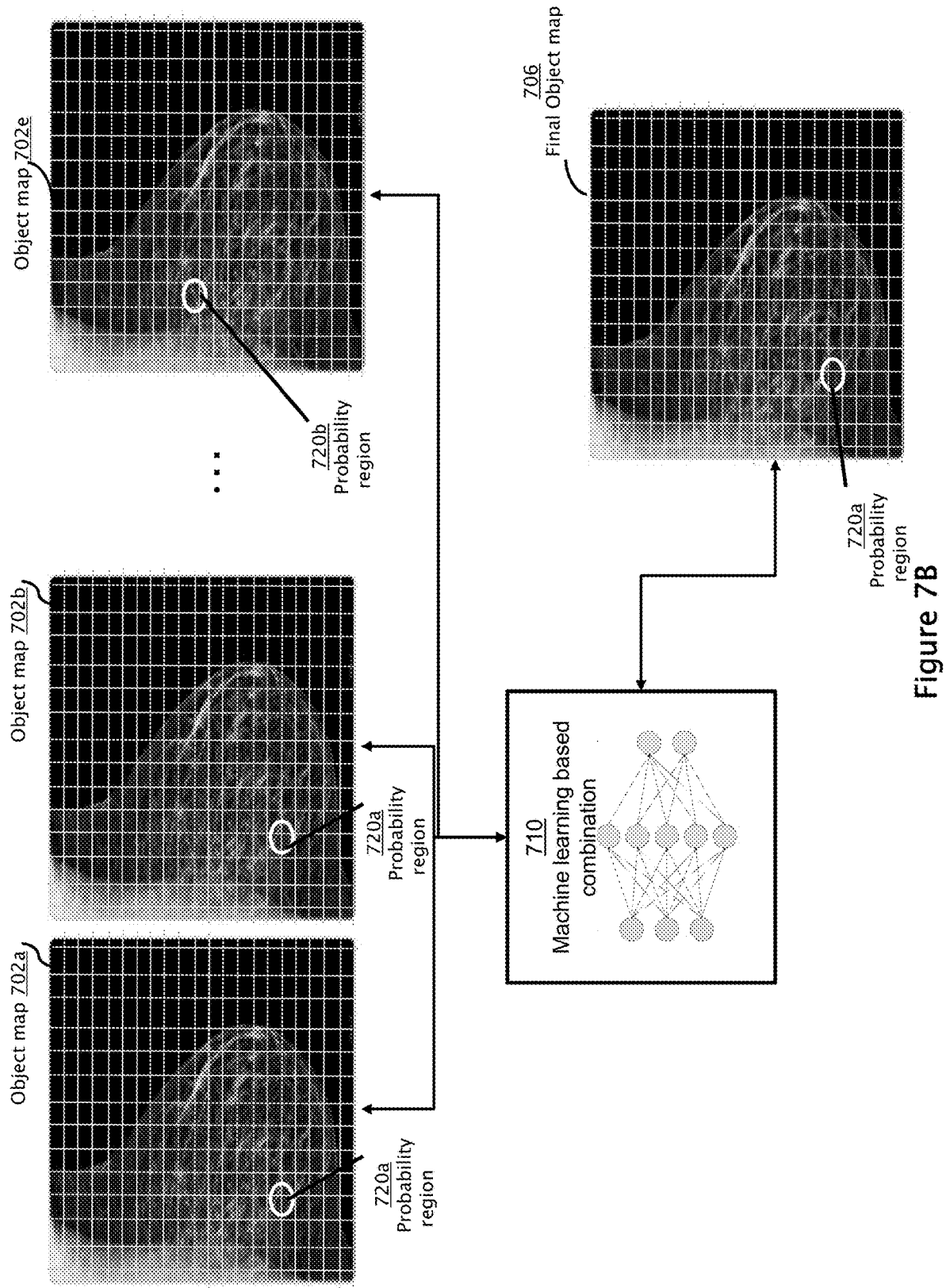

SYSTEM AND METHOD FOR HIERARCHICAL MULTI-LEVEL FEATURE IMAGE SYNTHESIS AND REPRESENTATION

RELATED APPLICATIONS DATA

The present application is a National Phase entry under 35 U.S.C § 371 of International Patent Application No. PCT/US2018/024911, having an international filing date of Mar. 28, 2018, which claims the benefit under 35 U.S.C. § 119 to U.S. Provisional Patent Application Ser. No. 62/478,977, filed Mar. 30, 2017, which is incorporated by reference in its entirety into the present application.

FIELD

The presently disclosed inventions relate generally to breast imaging techniques such as tomosynthesis, and more specifically to systems and methods for obtaining, processing, synthesizing, storing and displaying a breast imaging data set or a subset thereof. In particular, the present disclosure relates to creating a high-dimensional grid by decomposing high-dimensional data to lower-dimensional data in order to identify objects to display in one or more synthesized images.

BACKGROUND

Mammography has long been used to screen for breast cancer and other abnormalities. Traditionally, mammograms have been formed on x-ray film. More recently, flat panel digital imagers have been introduced that acquire a mammogram in digital form, and thereby facilitate analysis and storage of the acquired image data, and to also provide other benefits. Further, substantial attention and technological development have been dedicated to obtaining three-dimensional images of the breast using methods such as breast tomosynthesis. In contrast to the 2D images generated by legacy mammography systems, breast tomosynthesis systems construct a 3D image volume from a series of 2D projection images, each projection image obtained at a different angular displacement of an x-ray source relative to the image detector as the x-ray source is scanned over the detector. The constructed 3D image volume is typically presented as a plurality of slices of image data, the slices being mathematically reconstructed on planes typically parallel to the imaging detector. The reconstructed tomosynthesis slices reduce or eliminate the problems caused by tissue overlap and structure noise present in single slice, two-dimensional mammography imaging, by permitting a user (e.g., a radiologist or other medical professional) to scroll through the image slices to view only the structures in that slice.

Imaging systems such as tomosynthesis systems have recently been developed for breast cancer screening and diagnosis. In particular, Hologic, Inc. (www.hologic.com) has developed a fused, multimode mammography/tomosynthesis system that acquires one or both types of mammogram and tomosynthesis images, either while the breast remains immobilized or in different compressions of the breast. Other companies have introduced systems that include tomosynthesis imaging; e.g., which do not include the ability to also acquire a mammogram in the same compression.

Examples of systems and methods that leverage existing medical expertise in order to facilitate, optionally, the transition to tomosynthesis technology are described in U.S. Pat. No. 7,760,924, which is hereby incorporated by reference in its entirety. In particular, U.S. Pat. No. 7,760,924 describes a method of generating a synthesized 2D image, which may optionally be displayed along with tomosynthesis projection or reconstructed images, in order to assist in screening and diagnosis.

The 2D synthesized image is designed to provide a concise representation of the 3D reconstruction slices, including any clinically important and meaningful information, such as abnormal lesions and normal breast structures, while representing in relevant part a traditional 2D image. There are many different types of lesions and breast structures, which may be defined as different types of image objects having different characteristics. For any given image object visible in the 3D volume data, it is important to maintain and enhance the image characteristics (e.g., microcalcifications, architectural distortions, etc.), as much as possible, onto the 2D synthesized image. To achieve the enhancement of the targeted image object, it is critical to accurately identify and represent the image object present in the 3D tomosynthesis data.

SUMMARY

In one embodiment of the disclosed inventions, a method for processing breast tissue image data includes obtaining image data of a patient's breast tissue, and processing the image data to generate a set of image slices that collectively depict the patient's breast tissue. One or more filters associated with a plurality of multi-level feature modules are then applied to each image slice, the multi-level feature modules being configured to and recognize at least one assigned feature of a high-dimensional object that may be present in the patient's breast tissue, wherein the method further includes at each multi-level feature module, generating a feature map depicting regions (if any) of the respective image slice having the at least one assigned feature. The generated feature maps are then combined into an object map, preferably by using a learning library-based combiner, wherein the object map indicates a probability that the respective high-dimensional object is present at a particular location of the image slice. The method may further include creating a 2D synthesized image identifying one or more high-dimensional objects based at least in part on object maps generated for a plurality of image slices.

These and other aspects and embodiments of the disclosed inventions are described in more detail below, in conjunction with the accompanying figures.

BRIEF DESCRIPTION OF THE FIGURES

The drawings illustrate the design and utility of embodiments of the disclosed inventions, in which similar elements are referred to by common reference numerals. These drawings are not necessarily drawn to scale. In order to better appreciate how the above-recited and other advantages and objects are obtained, a more particular description of the embodiments will be rendered, which are illustrated in the accompanying drawings. These drawings depict only typical embodiments of the disclosed inventions and are not therefore to be considered limiting of its scope.

FIGS. 7A and 7B illustrate exemplary combination techniques to combine data to form the object maps.

DETAILED DESCRIPTION OF THE ILLUSTRATED EMBODIMENTS

Figure 1:
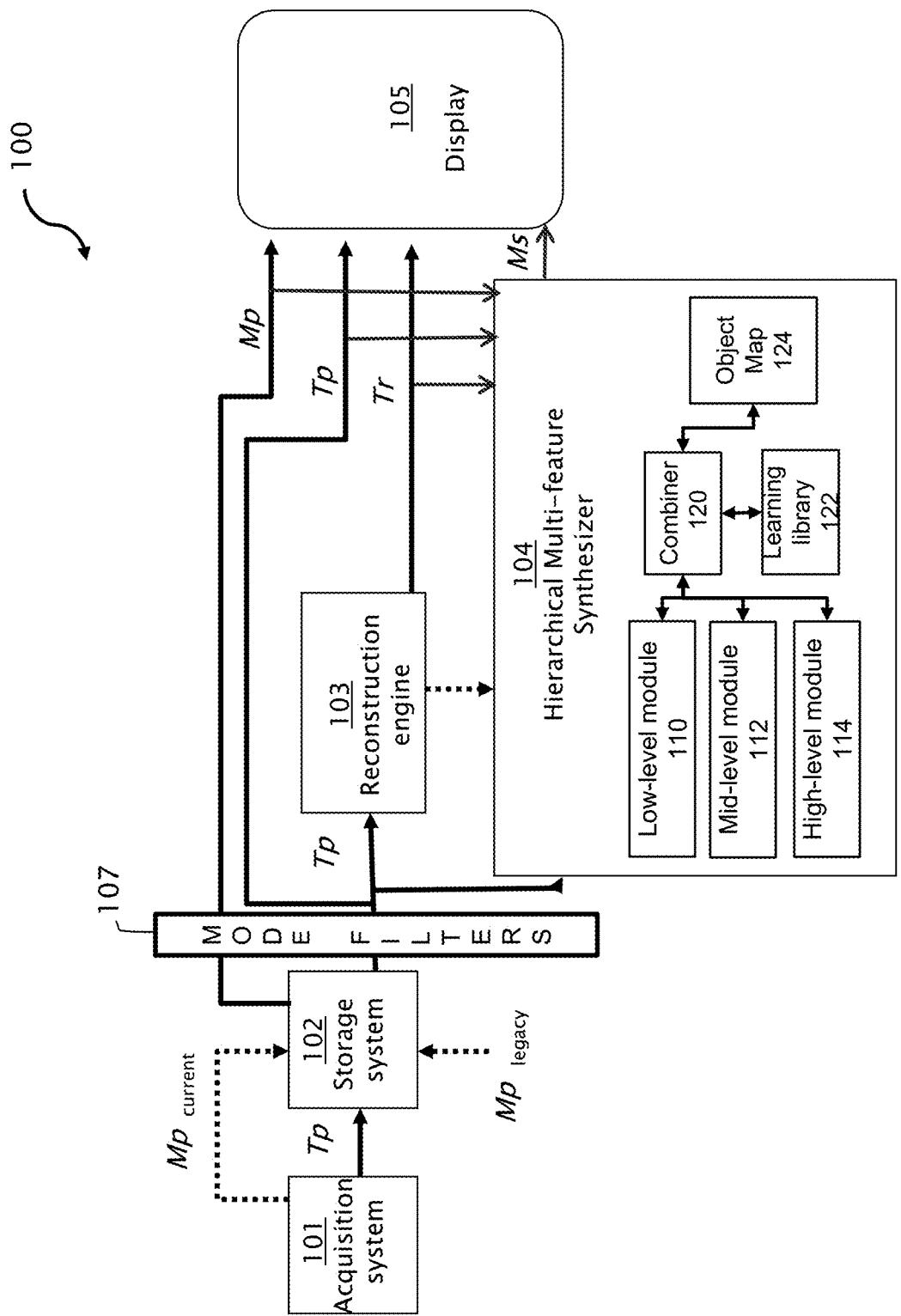
FIG. 1 is a block diagram illustrating the flow of data through an exemplary breast image acquisition and processing system in accordance with embodiments of the disclosed inventions.

All numeric values are herein assumed to be modified by the terms "about" or "approximately," whether or not explicitly indicated, wherein the terms "about" and "approximately" generally refer to a range of numbers that one of skill in the art would consider equivalent to the recited value (i.e., having the same function or result). In some instances, the terms "about" and "approximately" may include numbers that are rounded to the nearest significant figure. The recitation of numerical ranges by endpoints includes all numbers within that range (e.g., 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise. In describing the depicted embodiments of the disclosed inventions illustrated in the accompanying figures, specific terminology is employed for the sake of clarity and ease of description. However, the disclosure of this patent specification is not intended to be limited to the specific terminology so selected, and it is to be understood that each specific element includes all technical equivalents that operate in a similar manner. It is to be further understood that the various elements and/or features of different illustrative embodiments may be combined with each other and/or substituted for each other wherever possible within the scope of this disclosure and the appended claims.

Various embodiments of the disclosed inventions are described hereinafter with reference to the figures. It should be noted that the figures are not drawn to scale and that elements of similar structures or functions are represented by like reference numerals throughout the figures. It should also be noted that the figures are only intended to facilitate the description of the embodiments. They are not intended as an exhaustive description of the invention or as a limitation on the scope of the disclosed inventions, which is defined only by the appended claims and their equivalents. In addition, an illustrated embodiment of the disclosed inventions needs not have all the aspects or advantages shown. For example, an aspect or an advantage described in conjunction with a particular embodiment of the disclosed inventions is not necessarily limited to that embodiment and can be practiced in any other embodiments even if not so illustrated.

For the following defined terms and abbreviations, these definitions shall be applied throughout this patent specification and the accompanying claims, unless a different definition is given in the claims or elsewhere in this specification:

An "acquired image" refers to an image generated while visualizing a patient's tissue. Acquired images can be generated by radiation from a radiation source impacting on a radiation detector disposed on opposite sides of a patient's tissue, as in a conventional mammogram.

A "reconstructed image" refers to an image generated from data derived from a plurality of acquired images. A reconstructed image simulates an acquired image not included in the plurality of acquired images.

A "synthesized image" refers to an artificial image generated from data derived from a plurality of acquired and/or reconstructed images. A synthesized image includes elements (e.g., objects and regions) from the acquired and/or reconstructed images, but does not necessarily correspond to an image that can be acquired during visualization. Synthesized images are constructed analysis tools.

An "Mp" image is a conventional mammogram or contrast enhanced mammogram, which are two-dimensional (2D) projection images of a breast, and encompasses both a digital image as acquired by a flat panel detector or another imaging device, and the image after conventional processing to prepare it for display (e.g., to a health professional), storage (e.g., in the PACS system of a hospital), and/or other use.

A "Tp" image is an image that is similarly two-dimensional (2D), but is acquired at a respective tomosynthesis angle between the breast and the origin of the imaging x rays (typically the focal spot of an x-ray tube), and encompasses the image as acquired, as well as the image data after being processed for display, storage, and/or other use.

A "Tr" image is type (or subset) of a reconstructed image that is reconstructed from tomosynthesis projection images Tp, for example, in the manner described in one or more of U.S. Pat. Nos. 7,577,282, 7,606,801, 7,760,924, and 8,571,289, the disclosures of which are fully incorporated by reference herein in their entirety, wherein a Tr image represents a slice of the breast as it would appear in a projection x ray image of that slice at any desired angle, not only at an angle used for acquiring Tp or Mp images.

An "Ms" image is a type (or subset) of a synthesized image, in particular, a synthesized 2D projection image that simulates mammography images, such as a craniocaudal (CC) or mediolateral oblique (MLO) images, and is constructed using tomosynthesis projection images Tp, tomosynthesis reconstructed images Tr, or a combination thereof. Ms images may be provided for display to a health professional or for storage in the PACS system of a hospital or another institution. Examples of methods that may be used to generate Ms images are described in the above-incorporated U.S. Pat. Nos. 7,760,924 and 8,571,289.

It should be appreciated that Tp, Tr, Ms and Mp image data encompasses information, in whatever form, that is sufficient to describe the respective image for display, further processing, or storage. The respective Mp, Ms. Tp and Tr images are typically provided in digital form prior to being displayed, with each image being defined by information that identifies the properties of each pixel in a two-dimensional array of pixels. The pixel values typically relate to respective measured, estimated, or computed responses to X-rays of corresponding volumes in the breast, i.e., voxels or columns of tissue. In a preferred embodiment, the geometry of the tomosynthesis images (Tr and Tp) and mammography images (Ms and Mp) are matched to a common coordinate system, as described in U.S. Pat. No. 7,702,142. Unless otherwise specified, such coordinate system matching is assumed to be implemented with respect to the embodiments described in the ensuing detailed description of this patent specification.

The terms "generating an image" and "transmitting an image" respectively refer to generating and transmitting information that is sufficient to describe the image for display. The generated and transmitted information is typically digital information.

In order to ensure that a synthesized 2D image displayed to an end-user (e.g., an Ms image) includes the most clinically relevant information, it is necessary to detect and identify three-dimensional (3D) objects, such as malignant breast mass, tumors, etc., within the breast tissue. This information may be used to create a high-dimensional grid, e.g., a 3D grid, that helps create a more accurate and enhanced rendering of the most important features in the synthesized 2D image. The present disclosure describes one approach for creating a 3D grid by decomposing high-dimensional objects (i.e., 3D or higher) into lower-dimensional image patterns (2D images). When these 2D image patterns are detected in a tomosynthesis stack of images, they may be combined using a learning library that determines a location and morphology of the corresponding 3D object within the patient's breast tissue. This information regarding the presence of the respective 3D object(s) enables the system to render a more accurate synthesized 2D image to an end-user.

FIG. 1 illustrates the flow of data in an exemplary image generation and display system 100, which incorporates each of synthesized image generation, object identification, and display technology. It should be understood that, while FIG. 1 illustrates a particular embodiment of a flow diagram with certain processes taking place in a particular serial order or in parallel, the claims and various other embodiments described herein are not limited to the performance of the image processing steps in any particular order, unless so specified.

More particularly, the image generation and display system 100 includes an image acquisition system 101 that acquires tomosynthesis image data for generating Tp images of a patient's breasts, using the respective three-dimensional and/or tomosynthesis acquisition methods of any of the currently available systems. If the acquisition system is a combined tomosynthesis/mammography system, Mp images may also be generated. Some dedicated tomosynthesis systems or combined tomosynthesis/mammography systems may be adapted to accept and store legacy mammogram images, (indicated by a dashed line and legend "$Mp_{legacy}$" in FIG. 1) in a storage device 102, which is preferably a DICOM-compliant Picture Archiving and Communication System (PACS) storage device. Following acquisition, the tomosynthesis projection images Tp may also be transmitted to the storage device 102 (as shown in FIG. 1). The storage device 102 may further store a library of known 3D objects that may be used to identify significant 3D image patterns to the end-user. In other embodiments, a separate dedicated storage device (not shown) may be used to store the library of known 3D objects with which to identify 3D image patterns or objects.

The Tp images are transmitted from either the acquisition system 101, or from the storage device 102, or both, to a computer system configured as a reconstruction engine 103 that reconstructs the Tp images into reconstructed image "slices" Tr, representing breast slices of selected thickness and at selected orientations, as disclosed in the above-incorporated patents and applications.

Mode filters 107 are disposed between image acquisition and image display. The filters 107 may additionally include customized filters for each type of image (i.e., Tp, Mp, and Tr images) arranged to identify and highlight certain aspects of the respective image types. In this manner, each imaging mode can be tuned or configured in an optimal way for a specific purpose. For example, filters programmed for recognizing objects across various 2D image slices may be applied in order to detect image patterns that may belong to a particular high-dimensional objects. The tuning or configuration may be automatic, based on the type of the image, or may be defined by manual input, for example through a user interface coupled to a display. In the illustrated embodiment of FIG. 1, the mode filters 107 are selected to highlight particular characteristics of the images that are best displayed in respective imaging modes, for example, geared towards identifying objects, highlighting masses or calcifications, identifying certain image patterns that may be constructed into a 3D object, or for creating 2D synthesized images (described below). Although FIG. 1 illustrates only one mode filter 107, it should be appreciated that any number of mode filters may be utilized in order to identify structures of interest in the breast tissue.

The imaging and display system 100 further includes a hierarchical multi-level feature 2D synthesizer 104 that operates substantially in parallel with the reconstruction engine 103 for generating 2D synthesized images using a combination of one or more Tp, Mp, and/or Tr images. The hierarchical multi-level feature 2D synthesizer 104 consumes a set of input images (e.g., Mp, Tr and/or Tp images), determines a set of most relevant features from each of the input images, and outputs one or more synthesized 2D images. The synthesized 2D image represents a consolidated synthesized image that condenses significant portions of various slices onto one image. This provides an end-user (e.g., medical personnel, radiologist, etc.) with the most clinically-relevant image data in an efficient manner, and reduces time spent on other images that may not have significant data.

One type of relevant image data to highlight in the synthesized 2D images would be relevant objects found across one or more Mp, Tr and/or Tp images. Rather than simply assessing image patterns of interest in each of the 2D image slices, it may be helpful to determine whether any of the 2D image patterns of interest belong to a larger high-dimensional structure, and if so, to combine the identified 2D image patterns into a higher-dimensional structure. This approach has several advantages, but in particular, by identifying high-dimensional structures across various slices/depths of the breast tissue, the end-user may be better informed as to the presence of a potentially significant structure that may not be easily visible in various 2D slices of the breast.

Further, instead of identifying similar image patterns in two 2D slices (that are perhaps adjacent to each other), and determining whether or not to highlight image data from one or both of the 2D slices, identifying both image patterns as belonging to the same high-dimensional structure may allow the system to make a more accurate assessment pertaining to the nature of the structure, and consequently provide significantly more valuable information to the end-user. Also, by identifying the high-dimensional structure, the structure can be more accurately depicted on the synthesized 2D image. Yet another advantage of identifying high-dimensional structures within the various captured 2D slices of the breast tissue relates to identifying a possible size/scope of the identified higher-dimensional structure. For example, once a structure has been identified, previously unremarkable image patterns that are somewhat proximate to the high-dimensional structure may now be identified as belonging to the same structure. This may provide the end-user with an indication that the high-dimensional structure is increasing in size/scope.

To this end, the hierarchical multi-level feature 2D synthesizer 104 creates, for a stack of image slices, a stack of object maps indicating possible locations of 3D objects. In other words, the stack of object maps depicts one or more probability regions that possibly contain high-dimensional objects. In some embodiments, the set of object maps may be used to create a high-dimensional object grid (e.g., a 3D object grid) comprising one or more high-dimensional structures (3D objects) present in the breast tissue. The stack of object maps represents a 3D volume representative of the patient's breast tissue, and identifies locations that probably hold identified 3D object(s).

However, creating object maps that identify probabilities associated with the presence of known high-dimensional objects is difficult because it may be difficult to ascertain whether a structure is an independent structure, or whether it belongs to a high-dimensional structure. Also, it may be computationally difficult and expensive to run complex algorithms to identify complicated image patterns contains in the various image slices, and identify certain image patterns as belonging to a known object. To this end, high-dimensional objects may be decomposed into lower-dimensional image patterns.

This may be achieved through a plurality of hierarchical multi-level feature modules that decompose high-dimensional objects into simpler low-level patterns. In other words, an image pattern constituting a high-level object representation can be decomposed into multiple features such as density, shape, morphology, margin, edge, line, etc. as will be described in further detail below. These decomposed representations may be computationally easier to process than the original high-level image pattern, and may help associate the lower-level image patterns as belonging to the higher-dimensional object By decomposing more complex objects into simpler image patterns, the system enables easier detection of complex objects because it may be computationally easier to detect low-level features, while at the same time associating the low-level features to the high-dimensional object.

A high-dimensional object may refer to any object that comprises at least three or more dimensions (e.g., 3D object or higher, 3D object and time dimension, etc.). An image object may be defined as a certain type of image pattern that exists in the image data. The object may be a simple round object in a 3D space, and a corresponding flat round object in a 2D space. It can be an object with complex patterns and complex shapes, and it can be of any size or dimension. The concept of an object may extend past a locally bound geometrical object. Rather, the image object may refer to an abstract pattern or structure that can exist in any dimensional shape. It should be appreciated that this disclosure is not limited to 3D objects and/or structures, and may refer to even higher-dimensional structures. However, for simplicity, the remaining disclosure will refer to the higher-dimensional objects as 3D objects populated in a 3D grid.

The multi-level feature modules include a high-level feature module 114 to detect and identify higher-dimensional objects. For example, the high-level feature module 114 is configured to identify complex structures, such as a spiculated mass. However, it should be appreciated that the high-level feature module may require the most computational resources, and may require more complex algorithms that are programmed with a large number of filters or more computationally complex filters. Thus, in addition to directly utilizing a high-level feature module to recognize the complex structure, the 3D object may be decomposed into a range of mid-level and low-level features. Towards this end, the multi-level feature modules also include a mid-level feature module 112 configured to detect an image pattern of medium complexity, such as a center region of the spiculated mass, and a low-level feature module 110 configured to detect an even simpler image pattern, such as linear patterns radiating from the center of the spiculated mass.

Each of the multi-level feature modules (110, 112 and 114) may correspond to respective filters that comprise models, templates, and filters that enable each of the multi-level feature modules to identify respective image patterns. These multi-level feature modules are run on the input images (e.g., Tp, Tr, Mp, etc.) with their corresponding filters to identify the assigned high-level, mid-level and/or low-level features. Each hierarchical multi-level feature module (e.g., 110, 112 and 114) outputs a group of feature maps identifying areas of the respective image slice that comprise that particular feature. For example, the low-level feature module 110 may identify areas of the image slice that contains lines. The mid-level feature module 112 may identify areas of the image slice that contains circular shapes, and the high-level feature module 114 may identify areas containing the entire spiculated mass.

These feature maps outputted by the respective feature module may be combined using a combiner 120. The combiner 120 may be any kind of suitable combiner, e.g., a simple voting-based combiner such as shown in FIG. 7A, or a more complicated learning library-based combiner 122, such as shown in FIGS. 1 and 7B. In particular, the learning library-based combiner 120/122 generates a series of object maps 124 corresponding to each image slice, wherein the series of object maps represent the 3D volume of the patient's breast tissue and identify possible areas that contain 3D objects. In some embodiments, the stack of object maps may be utilized to create a 3D grid that identifies objects in a 3D coordinate space.

The learning library-based combiner 120/122 stores a set of known shapes/image patterns, and uses the feature maps to determine a probability of whether a particular shape exists at a 3D location. Each object map 124 is formed based on combining the various feature maps derived through the feature modules. It should be appreciated that the formed object maps 124 may identify probabilities corresponding to multiple different objects, or may simply identify probabilities corresponding to a single object. In other words, a single object map 124 corresponding to a particular image slice may identify a possible location for two different objects. Or, a single object map 124 may identify two possible locations for the same object. Thus, multiple feature maps belonging to one or more high-dimensional objects may be combined into a single object map. The hierarchical multi-level feature synthesizer 104 utilizes the stack of object maps 124, in addition to the input images (e.g., Tr, Tp, Mp, etc.) in order to create one or more synthesized 2D images, as will be discussed in further detail below.

The synthesized 2D images may be viewed at a display system 105. The reconstruction engine 103 and 2D synthesizer 104 are preferably connected to a display system 105 via a fast transmission link. The display system 105 may be part of a standard acquisition workstation (e.g., of acquisition system 101), or of a standard (multi-display) review station (not shown) that is physically remote from the acquisition system 101. In some embodiments, a display connected via a communication network may be used, for example, a display of a personal computer or of a so-called tablet, smart phone or other hand-held device. In any event, the display 105 of the system is preferably able to display respective Ms, Mp, Tr, and/or Tp images concurrently, e.g., in separate side-by-side monitors of a review workstation, although the invention may still be implemented with a single display monitor, by toggling between images.

Thus, the imaging and display system 100, which is described as for purposes of illustration and not limitation, is capable of receiving and selectively displaying tomosynthesis projection images Tp, tomosynthesis reconstruction images Tr, synthesized mammogram images Ms, and/or mammogram (including contrast mammogram) images Mp, or any one or sub combination of these image types. The system 100 employs software to convert (i.e., reconstruct) tomosynthesis images Tp into images Tr, software for synthesizing mammogram images Ms, software for decomposing 3D objects, software for creating feature maps and object maps. An object of interest or feature in a source image may be considered a 'most relevant' feature for inclusion in a 2D synthesized image based upon the application of the object maps along with one or more algorithms and/or heuristics, wherein the algorithms assign numerical values, weights or thresholds, to pixels or regions of the respective source images based upon identified/detected objects and features of interest within the respective region or between features. The objects and features of interest may include, for example, spiculated lesions, calcifications, and the like.

Figure 2:
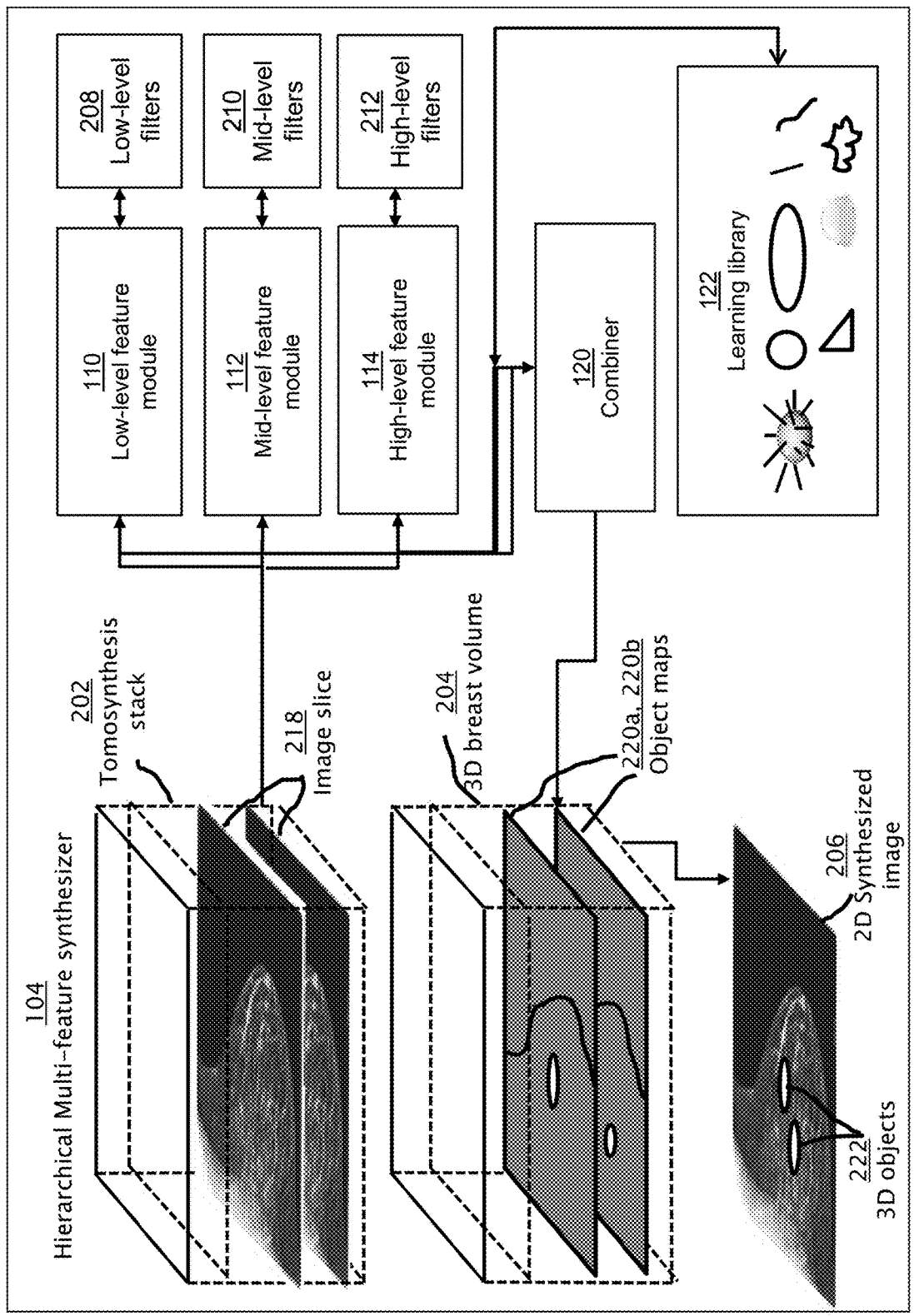
FIG. 2 is a block diagram illustrating the flow of data through a hierarchical multi-level feature synthesizer in accordance with embodiments of the disclosed inventions.

FIG. 2 illustrates the hierarchical multi-level feature synthesizer 104 in further detail. As discussed above, various image slices 218 of a tomosynthesis data set (or "stack") 202 (e.g., filtered and/or unfiltered Mp, Tr and/or Tp images of a patient's breast tissue) are directed to the hierarchical multi-level feature synthesizer 104, which are then processed to determine portions of the images to highlight in a synthesized 2D image that will be displayed on the display 105. The image slices 218 may be consecutively-captured cross-sections of a patient's breast tissue. Or, the image slices 218 may be cross-sectional images of the patient's breast tissue captured at known intervals. The tomosynthesis image stack 202 comprising the image slices 218 may be forwarded to the hierarchical multi-level feature synthesizer 104, which evaluates each of the source images in order to (1) identify high-dimensional object(s) 222 that may be identified in the image data set (Tr) for possible inclusion in one or more 2D synthesized images, and/or (2) identify respective pixel regions in the images that contain the identified object(s) 222.

As shown in the illustrated embodiment, the tomosynthesis stack 202 comprises a plurality of images 218 taken at various depths/cross-sections of the patient's breast tissue. Some of the images 218 in the tomosynthesis stack 202 comprise 2D image patterns. Tus, the tomosynthesis stack 202 comprises a large number of input images containing various image patterns within the images of the stack. For example, the tomosynthesis stack 202 may comprise one hundred images 218 captured at various depths/cross sections of the patient's breast tissue. Only a few of the images 218 may comprise any information of significance. Also, it should be noted that the tomosynthesis stack 202 simply contains 2D image patterns at various image slices 218, but it may be difficult to determine 3D structures based on the various cross-sectional images. However, the tomosynthesis stack 202 may be utilized in order to create the 3D breast volume 204 comprising the stack of object maps 124 (indicated by reference numbers 220a and 220b in FIG. 2, as explained in greater detail below).

The 3D breast volume 204 may be considered a 3D coordinate space representing a patient's breast mass. Rather than depicting 2D image patterns at various image slices, the 3D breast volume 204 depicts, through the object maps 124 (220a, 220b), probable locations of identified 3D objects in the entire mass (or portion thereof) that represents the patient's breast tissue. The object maps 214 (220a, 220b) depict, for each image slice 218, a probability that a particular object (or objects) 222 is/are present at that particular coordinate location. Rather the simply display image patterns, the stack of object maps clearly identifies particular objects in the breast volume 204. This allows for more accurate rendering of the 2D synthesized image 206 that can depict locations of objects 222 rather than simply highlight interesting image patterns (that may or may not be related to objects). Knowing that image patterns belong to particular objects 222 provides the end-user with more insight when reviewing the synthesized 2D image 206.

The object maps 124 (220a, 220b) may comprise several areas depicting a probability that an object is present at that location. For example, in the illustrated embodiment, two object maps, 220a and 220b, are shown depicting probabilities for objects at two different locations. These may refer to a single object or multiple objects, as discussed above.

The object maps 220a and 220b are created by running the image slices 218 through the various hierarchical multi-level feature modules (e.g., modules 110, 112 and 114) to produce feature maps that are then combined together in consultation with the learning library-based combiner 120/122 to determine a possible location of the respective 3D object. It should be appreciated that each 3D object may correspond to respective high-level, mid-level and low-level feature modules. Each of the multi-level feature modules outputs feature maps that identify the particular feature in the image slice. Multiple feature maps may be combined using the learning-library-based combiner 120/122 to generate an object map 220a, 220b for a particular image slice 218.

For example, in the illustrated embodiment, object maps 220a and 220b may depict probabilities for two separate objects. Although not necessarily visible in the displayed object maps 220a, 220b, themselves, when these object maps 220a and 220b are viewed as a whole for the entire tomosynthesis stack 202, the shape/size and dimensions of the various objects will become clear in the 3D breast volume 204. Thus, since two objects 222 are identified in the 3D breast volume 204, the 2D synthesized image 206 identifies their locations. It should be appreciated, however, that these two identified objects 222 may be the same object or may be multiple objects. In particular, it should be appreciated that these objects 222 may be predefined objects that the system has been trained to identify. However, even in healthy breast tissue that does not necessarily comprise any suspicious objects or structures, the 3D breast volume 204 may display a breast background object. For example, all breast linear tissue and density tissue structures can be displayed as the breast background object. For example, the 3D object grid 204 may display a "breast background" pattern throughout the 3D grid, and one or more objects may be located at various areas of the breast background. In other embodiments, "healthy" objects such as spherical shapes, oval shapes, etc., may simply be identified through the 3D object grid 204. These identified 3D objects may then be displayed on the 2D synthesized image 206; of course, out of all identified 2D objects, more clinically-significant objects may be prioritized or otherwise enhanced when displaying the respective object on the 2D synthesized image, as will be discussed in further detail below.

In one or more embodiments, the hierarchical multi-level feature synthesizer 104 utilizes both the tomosynthesis image stack 202 along with the created 3D breast volume 204 containing the stack of object maps 220 in order to condense the relevant features into a single 2D synthesized image 206. As shown in the illustrated embodiment, the 2D synthesized image 206 provides important details from multiple image slices on a single 2D synthesized image 206. Simply utilizing legacy techniques on the tomosynthesis image stack 202 may or may not necessarily provide details about both identified objects. To explain, if there is overlap in the z direction of two important image patterns, the two image patterns are essentially competing with each other for highlighting in the 2D synthesized image. If it is not determined that the two image patterns belong to two separate objects, important aspects of both objects may be compromised. Alternatively, only one of the two structures may be highlighted at all in the 2D synthesized image 206. Or, in yet another scenario, the 2D synthesized image may depict both structures as one amorphous structure such that an important structure goes entirely undetected by the end-user.

Thus, identifying objects through the stack of object maps 220a, 220b, allows the system to depict the structures more accurately in the 2D synthesized image 206, and allows for various objects to be depicted simultaneously, even if there is an overlap of various objects in the coordinate space. Thus, utilizing the 3D breast volume 204 containing the stack of object maps 220a, 220b has many advantages in producing a more accurate 2D synthesized image 206.

In one or more embodiments, the tomosynthesis image stack 202 may be used to construct the 3D breast volume 204, as discussed above. The various images of the tomosynthesis image stack 202 may be run through the multi-level feature modules (e.g., modules 110, 112 and 114). More specifically, the tomosynthesis image stack 202 may be run through a high-level module 114 that is configured to identify complex structures. For example, the high-level module 114 corresponding to 3D spiculated masses may be configured to identify the entire spiculated lesion, or complex sub-portions of spiculated lesions. The high-level module 114 may be associated with high-level filters 212 that comprise models, templates and filters that allow the high-level feature module 114 to detect the assigned feature. Although the illustrated embodiment only depicts a single high-level, mid-level and low-level feature, it should be appreciated that there may be many more multi-level feature modules per object. For example, there may be separate high-level, mid-level and low-level modules for each of the two objects depicted in the 2D synthesized image 206.

The tomosynthesis image stack 202 may also be run through the mid-level feature module 112 that may be configured to identify mid-level features. For example, the mid-level feature module 112 corresponding to 3D spiculated masses may detect circular structures representative of the centers of spiculated lesions. The mid-level feature module 112 may be associated with mid-level filters 210 that comprise models, templates and filters that allow the mid-level module 112 to detect the assigned feature.

Similarly, the tomosynthesis image stack 202 may also be run through the low-level feature module 110 that may be configured to identify much simpler low-level features. For example, the low-level feature module 110 corresponding to 3D spiculated masses may detect lines representative of linear patterns that radiate from the centers of spiculated lesions. The low-level feature module 110 may be associated with low-level filters 208 that comprise models, templates and filters that allow the low-level module 110 to detect the assigned feature.

As will be described in further detail below, each of the multi-level feature modules outputs a feature map showing areas that contain the particular feature on the image slice. These outputted feature maps for each image slice 218 may be combined using the learning library-based combiner 120/122. The learning library-based combiner 120/122 may store a plurality of known objects and may determine, based on the outputted feature maps, a probability that a particular object is located on the image slice 218. It should be appreciated that the learning library 122 will achieve greater accuracy over time, and may produce increasingly more accurate results in identifying both the location, scope and identity of respective objects 222.

The learning library-based combiner 120/122 synthesizes information gained through the various feature maps outputted by each of the hierarchical multi-level feature modules, and combines the feature maps into the object maps 220a, 220b. As discussed above, the series of object maps 220a and 220b forms the 3D breast volume 204.

Figure 3:
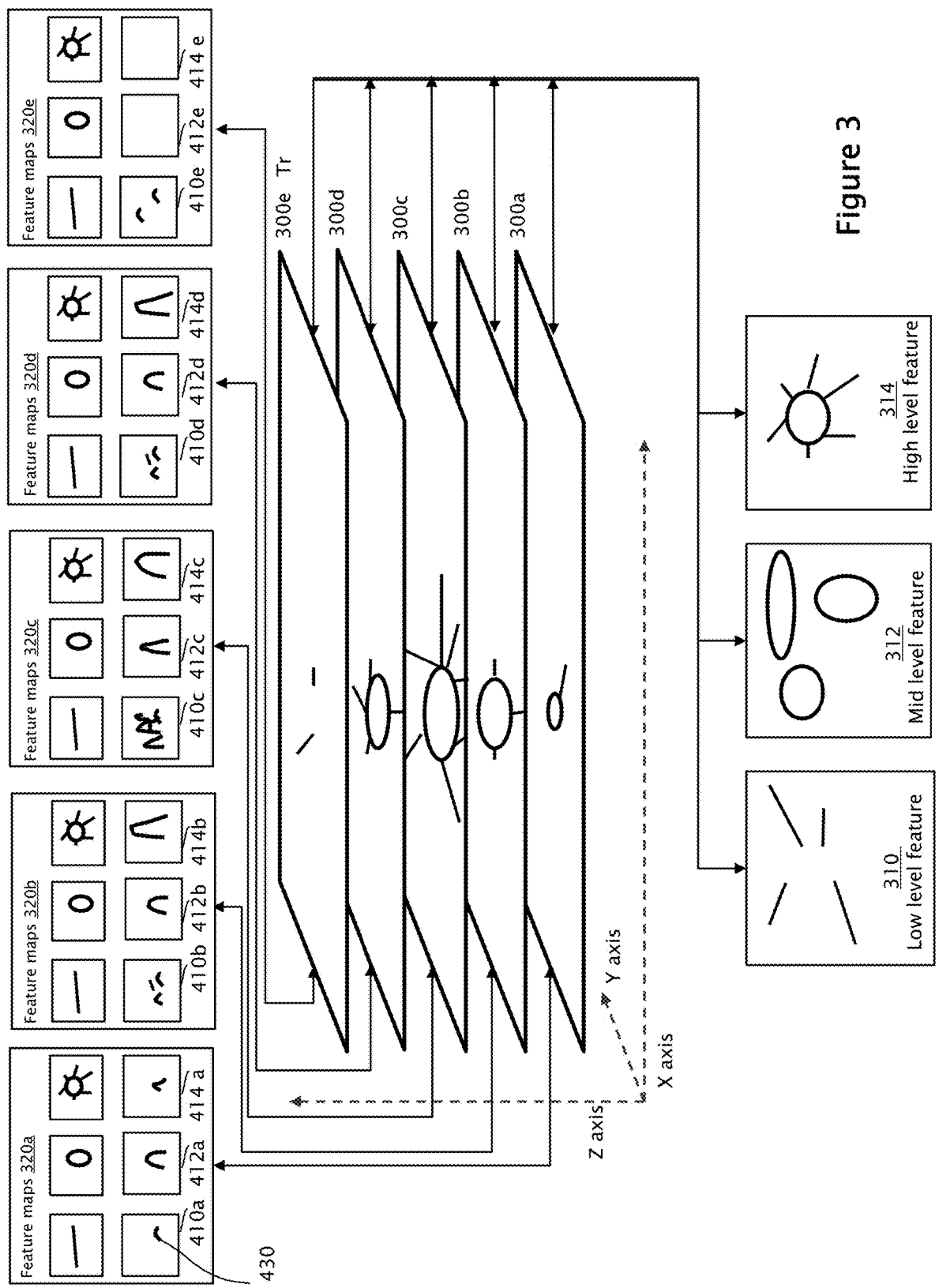
FIG. 3 illustrates one embodiment of running three multi-level feature modules associated with a high-dimensional object on a plurality of tomosynthesis images to generate a set of feature maps.

Referring now to FIG. 3, an example approach of running the various hierarchical multi-level feature modules on an example set of Tr slices is illustrated. In the illustrated embodiment, low-level feature module 310, mid-level feature module 312 and high-level feature module 314 are run on a set of Tr slices 300a-300e. Following the example from above, the low-level feature module 310 is configured to identify linear structures associated with a spiculated mass/lesion. The mid-level feature module 312 is configured to identify circular structures/arcs associated with spiculated lesions, and the high-level feature module 314 is configured to directly identify all, or almost all, spiculated lesions, i.e., structures having a spherical center as well as linear patterns emanating from the center.

When the multi-level feature modules (e.g., 310, 312 and 314) are run on the stack of Tr slices 300a-300e, a set of feature maps 320a-320e are generated. In one or more embodiments, at least three groups of feature maps (for each of the three modules) are generated for each Tr image slice. More specifically, referring to feature maps 320a, feature map 410a is generated based upon running the low-level feature module 310 (that identifies linear patterns) on Tr slice 300a. Similarly, feature map 412a is generated based upon running the mid-level feature module 312 (that identifies circular patterns) on Tr slice 300a, and feature map 414a is generated based upon running the high-level feature module 314 (that identifies the spiculated lesion) on Tr slice 300a.

Similarly, feature maps 320b (comprising 410b, 412b, and 414b) are generated by running the multi-level feature modules 310, 312 and 314 on Tr slice 300b; feature maps 320c (comprising 410c, 412c, and 414c) are generated by running the multi-level feature modules 310, 312 and 314 on Tr slice 300c; feature maps 320d (comprising 410d, 412d, and 414d) are generated by running the multi-level feature modules 310, 312 and 314 on Tr slice 300d; and feature maps 320e (comprising 410e, 412e, and 414e) are generated by running the multi-level feature modules 310, 312 and 314 on Tr slice 300e. Although not drawn to scale, each of the feature maps represents a respective coordinate system that identifies regions of the image slice containing the assigned feature.

For example, referring to feature map 410a, a highlighted region 430 refers to the possibility of a linear structure being present at that coordinate location of the Tr slice 300a. Similarly, the highlighted region of feature map 412a indicates areas containing a circular structure in Tr slice 300a, and the highlighted region of feature map 414a indicates an area that possibly contains an entire spiculated lesion is present in Tr slice 300a. As can be seen from the range of feature maps, some highlighted regions are denser than other highlighted regions. For example, feature map 414c shows a highlighted region indicating a strong possibility that a spiculated lesion is detected. Similarly, other feature maps (e.g., 410b, 410c, 410d, etc.) illustrate multiple regions indicating several detected features at various locations. If no feature is detected at a particular Tr image slice, the respective feature maps may show no highlighted regions (e.g., 412e and 414e).

Figure 4:
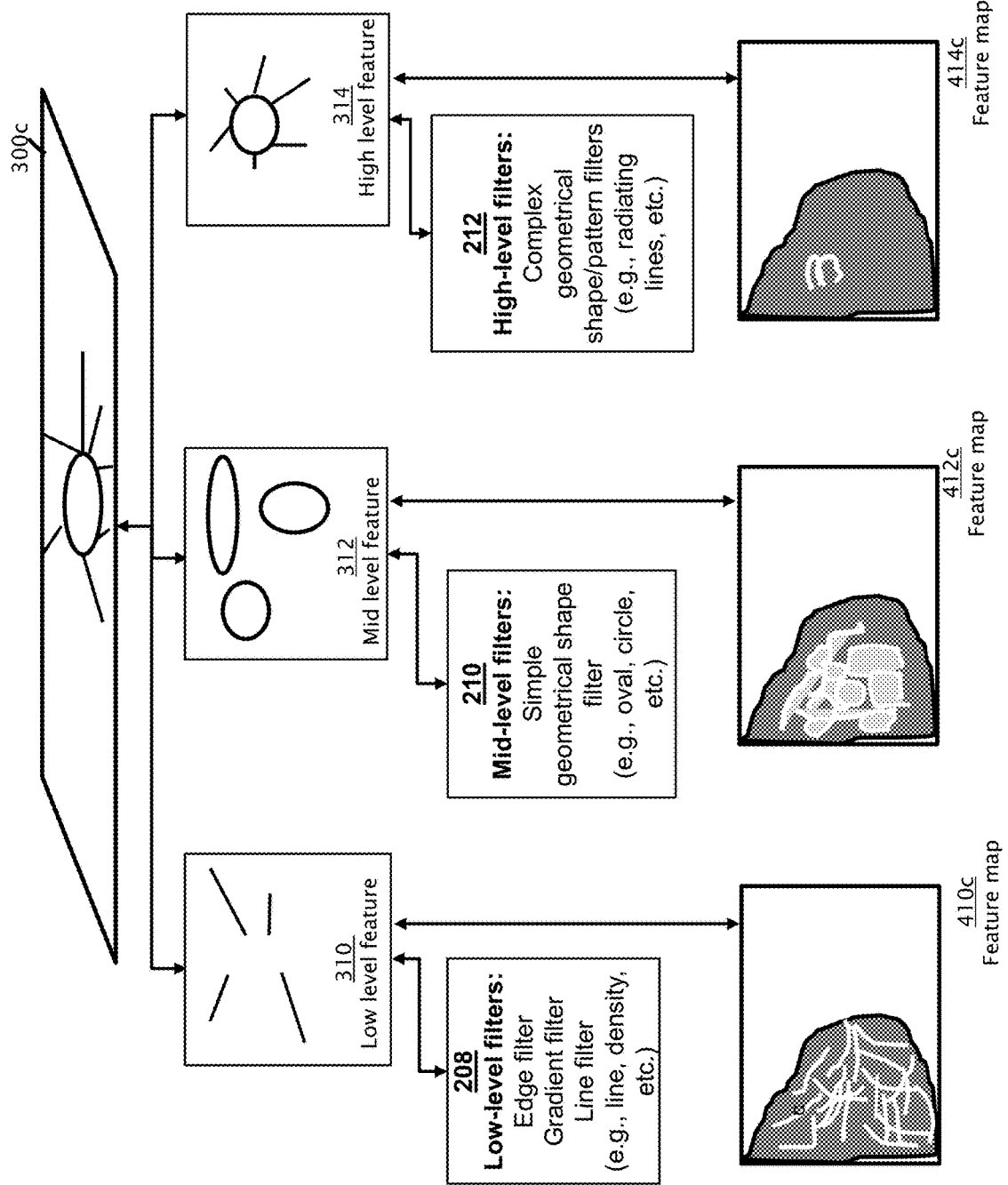
FIG. 4 illustrates one embodiment of applying filters associated with the three multi-level feature modules on one tomosynthesis image of the plurality of tomosynthesis images of FIG. 3 to generate three feature maps.

FIG. 4 illustrates an exemplary technique of running filters associated with each of the multi-level feature modules to generate respective feature maps. Specifically, FIG. 4 illustrates the low-level feature module 310, mid-level feature module 312 and high-level feature module 314, respectively, being run on Tr slice 300c. As discussed previously, each of the feature modules is associated with one or more filters, templates and/or models that enable the algorithms associate with the particular feature module to detect the respective shape and/or other characteristics associated with the feature module. In the illustrated embodiment, low-level feature module 310 may correspond to low-level filters 208. Although FIG. 4 describes only a few filters, it should be appreciated that any number of filters may be similarly used. Typically, the low-level filters 208 may be computationally less complex to run, and may use fewer filters and/or less complex filters when compared to the mid-level or high-level feature modules.

For example, edge filters may be used to detect edges in the image slice. Similarly, edge filters, line filters and shape filters may be used to detect linear patterns in the image slice 300c. Since the low-level module 310 is simply configured to detect linear patterns, these simple filters may be sufficient. When these filters are run on the image slice 300c, the feature map may record one or more regions that indicate a coordinate location of the line. Feature map 410c shows numerous regions of Tr slice 300c that comprise the low-level features (e.g., lines).

Similarly, the mid-level feature module 312 corresponds to the mid-level filters 210. In addition to (or instead of) the edge filters, gradient filters, line filters, and shape filters, the mid-level filter bank 210 may also comprise filters configured to recognize simple geometrical shapes. For example, the mid-level filters 210 may be configured to recognize a simple circular shape. In another embodiment, orthogonal direction filters may be configured that enable the system to determine whether an orthogonal direction of set of edges converge at a single center point. Such a combination of filters may be used to determine a region corresponding to a circular shape. The feature map 412c highlights regions comprising circular shapes present in image slice 300c.

The high-level feature module 314 corresponds to the high-level filters 212. In addition to (or instead of) filters described with respect to the low-level filters bank 208 and mid-level filters bank 210, the high-level filters 212 may comprise filters that are specifically trained to detect complex structures. These may be a combination of simple filters or more sophisticated image recognition algorithms that help detect a shape that most resembles a spiculated mass. It should be appreciated that these filters/algorithms may be computationally more complex as compared to the filters in the low-level and mid-level filters bank (e.g., 208 and 210 respectively). For example, in the illustrated embodiment, the high-level filters 208 may be configured to detect a complex geometrical shape, such as radiating lines around a circular shape. In the illustrated embodiment, the feature map 414c depicts regions of the image slice 300c containing the high-level feature. As discussed above, for each image slice, the feature maps corresponding to each of the multi-level feature modules (110, 112 and 114) are combined to form an object map depicting a probability that the particular object is present at a particular location of the image slice. The object maps are created using the learning library-based combiner 120/122, as discussed above.

Figure 5:
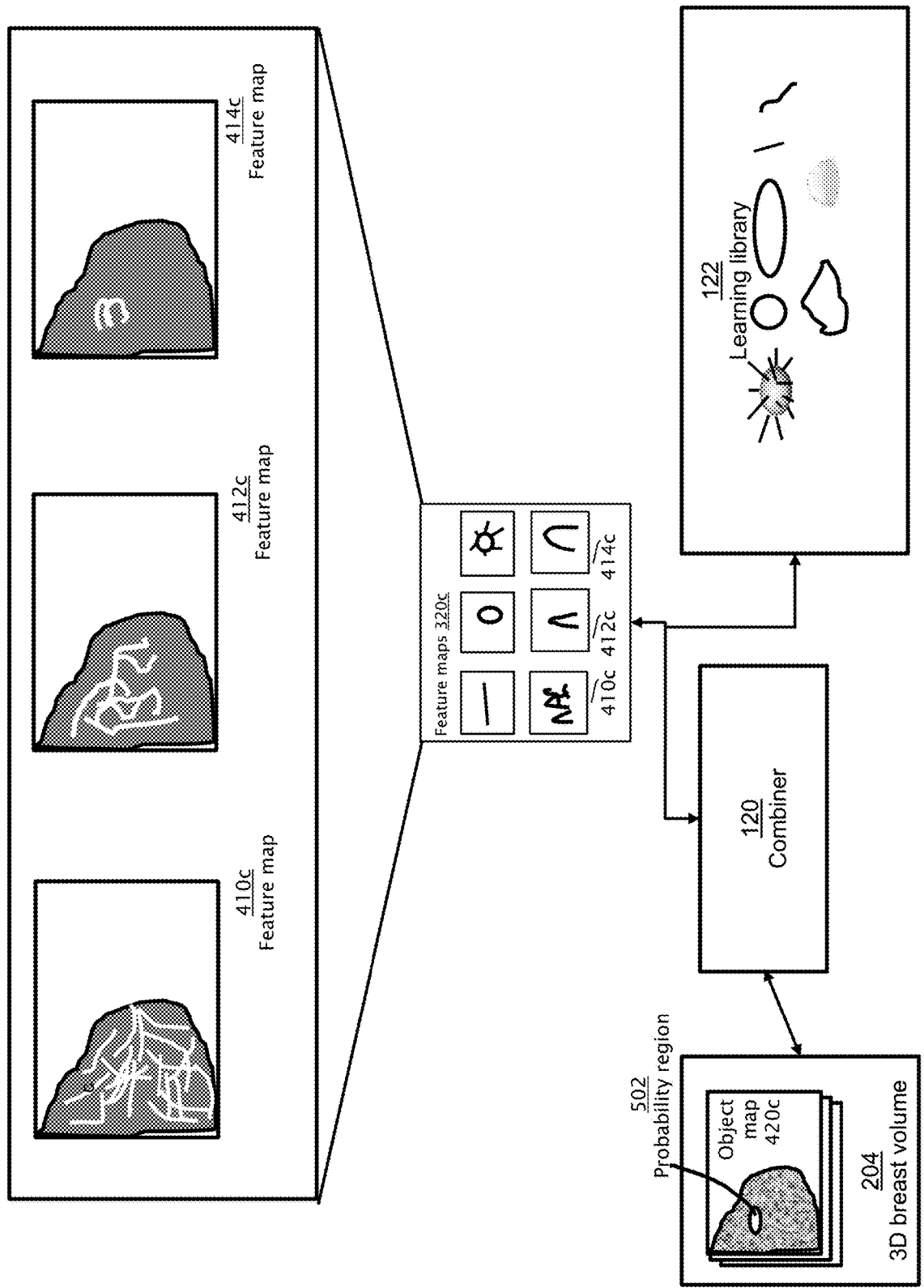
FIG. 5 illustrates one embodiment of combining feature maps into a single object map using a learning library.

FIG. 5 illustrates this combination process in further detail. In particular, FIG. 5 illustrates an exemplary approach for combining features detected through the various hierarchical multi-level feature modules is illustrated for image slice 300c. As shown in the illustrated embodiment, feature maps 410c, 412c and 414c have been created through each of the multi-level feature modules (310, 312 and 314) for image slice 300c. Although not shown in FIG. 5, similar feature maps may be generated for the other image slices 300a, 300b, 300d and 300e of FIG. 3. The feature maps 320c for image slice 300c are combined using the learning library-based combiner 120/122. In one or more embodiments, the learning library 122 uses machine learning techniques to improve accuracy of 3D shapes detected through the feature maps. Various machine learning algorithms may be utilized to combine information derived from the various multi-level feature modules and the feature maps to accurately generate an object map identifying a probable location of a 3D object.

The learning library-based combiner 120/122 may receive inputs from the three levels of feature maps regarding the presence of a spiculated mass. This pattern of information may help create an object map identifying a probability region 502 in the object map 420c. It should be appreciated that the technique described herein is simplified for illustrative purposes, and a number of complex machine learning algorithms may be used to accurately compute the probable location and dimensions of the 3D object. It should also be appreciated that machine learning algorithms employed as part of the learning library 122 may enable the system to detect and identify 3D objects using very little information as the system "learns" more over time. Thus, it is envisioned that the learning library 122 grows to be more efficient and accurate over time. For example, in one or more embodiments, weights may be assigned to feature maps derived through various feature modules in order for the system to gauge how much weight a particular feature module should be given. As the system "learns" more, the weights assigned to certain features may change.

As discussed above, the learning library-based combiner 120/122 combines information from the various feature maps in order to produce the object map 420c depicting the probability region 502 of a particular 3D object. For example, the probability region 502 may pertain to a location, size and scope of a spiculated mass that may be present in Tr image slice 300c. Similarly, the learning-library-based combiner 120/122 may output other object maps for the other image slices 300a, 300b, 300d and 300e (not shown). This stack of object maps may be used to create the 3D breast volume (such as 204 shown in FIG. 2), which helps identify one or more objects present at various 3D locations of the patient's breast tissue.

Figure 6B:
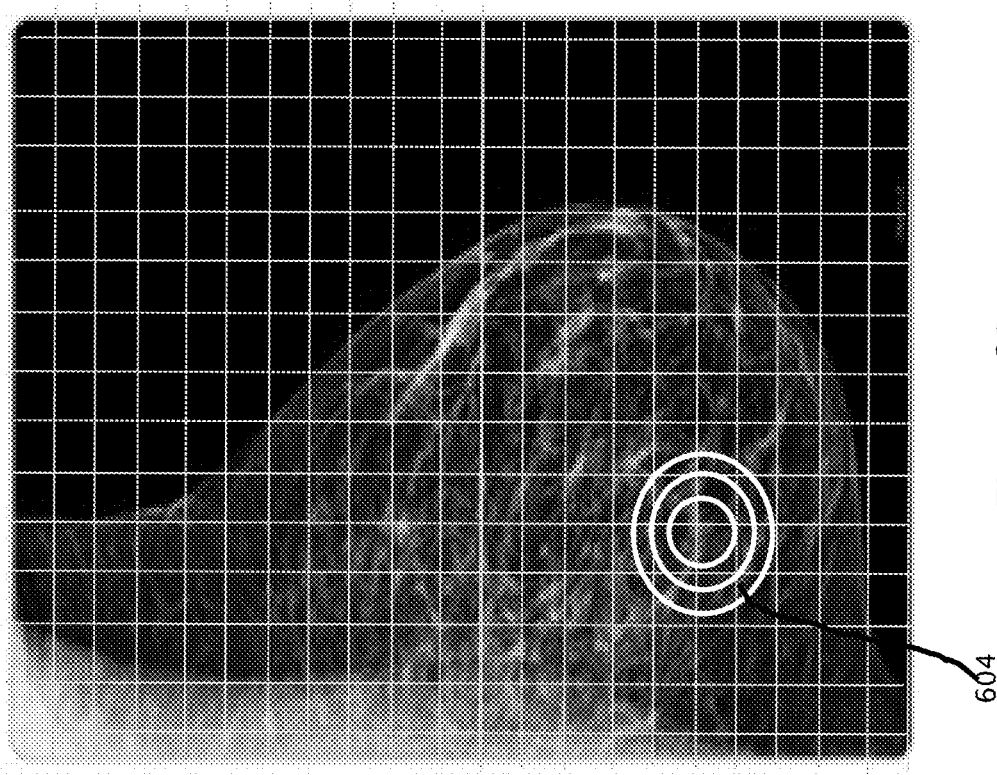
FIGS. 6A and 6B illustrate exemplary embodiments of displaying a feature on an object map.
Figure 6A:
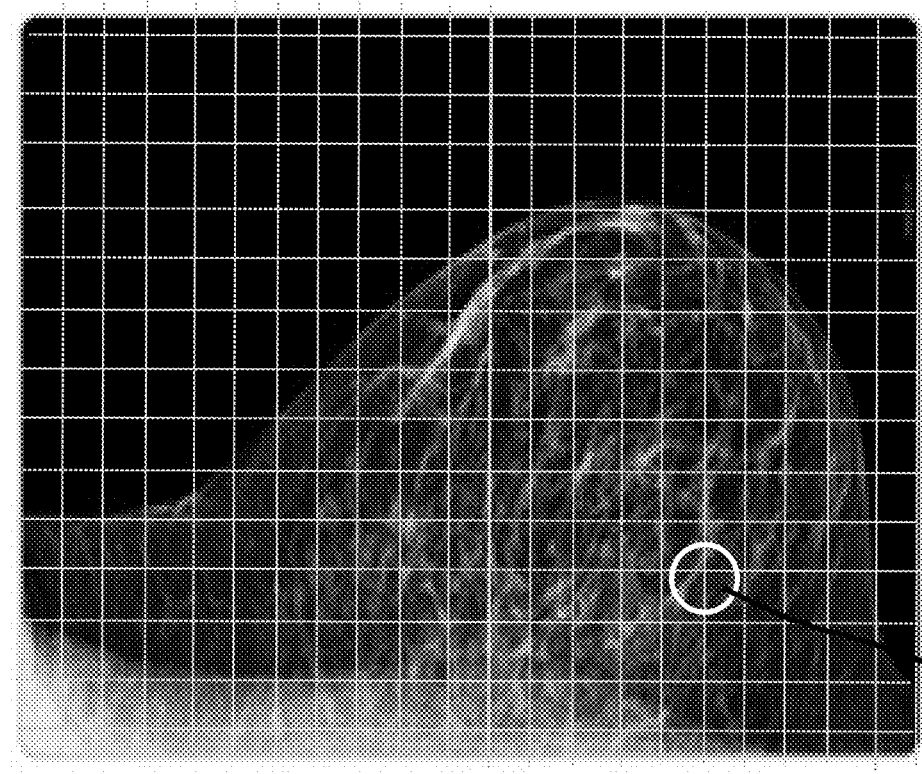

FIGS. 6A and 6B illustrate respective exemplary embodiments of depicting information on an object map. FIG. 6A simply illustrates a core of a particular object/feature of interest through a simple indicator 602, whereas FIG. 6B may provide more information through the object map by showing iso-contours of a detected object through indicator 604, which not only depicts a location of a particular object but also depicts probabilities of how large the object may be. For example, the probability that the object is at the center of indicator 604 may be the highest, and the largest circle of the indicator 704 may indicate a region of lower (but still significant) probability.

FIG. 7A illustrates an exemplary embodiment of how an alternative embodiment using a more simplified voting-based combiner 708 to determine a probability region corresponding to a 3D object in a final object map 704. In particular, the voting-based combiner 708 may be utilized on the object maps 702a-702e, so that the system "votes" on a first probability region 720a, shown in object map 702a and 702b, a second probability region 720b, shown in object map 702e, or both probability regions 720a and 720b. In the illustrated embodiment, the voting based combination may result in both probability regions 720a and 720b being highlighted in the final object map 704.

By contrast, FIG. 7B illustrates an example embodiment of the learning library-based combiner 710 to create the final object map 706. In the illustrated embodiment, even though probability object maps 702a-702e highlight different probability regions 720a and 720b (similar to the embodiment shown in FIG. 7A), a machine learning combination algorithm employed by the combiner 710 uses neural networks to select only one of the two probability regions 720a to be displayed in the final object map 706. As discussed above, when using neural networks, the system may become more sophisticated over time by "learning" patterns determined from various feature maps to construct more accurate object maps.

Figure 8:
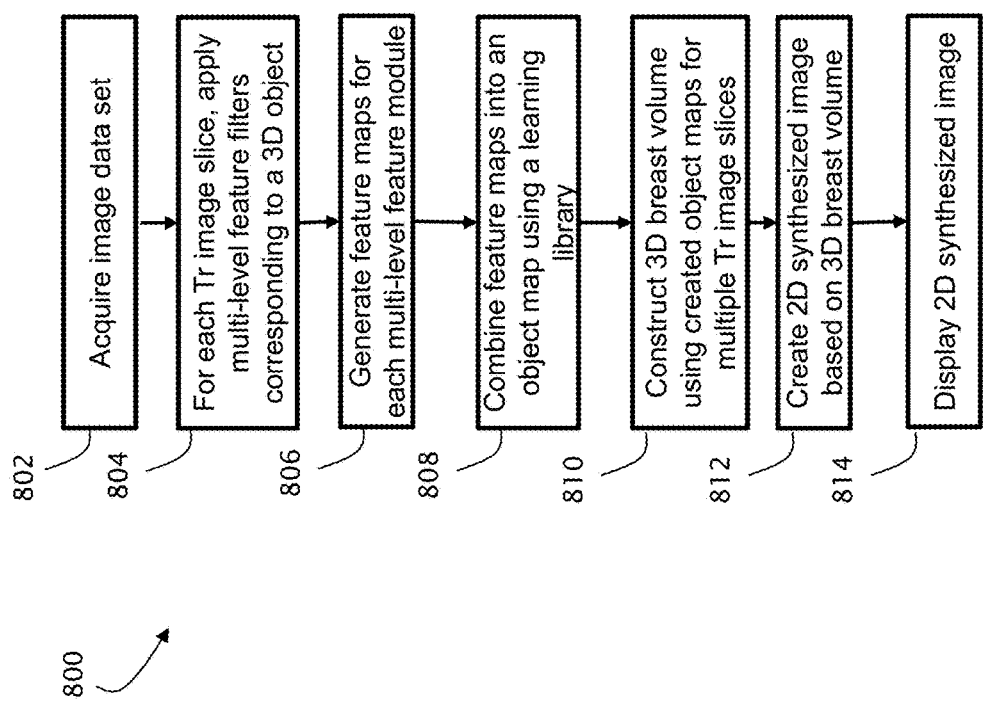
FIG. 8 illustrates an exemplary flow diagram depicting various steps to generate one or more synthesized 2D images using the high-dimensional grid.

FIG. 8 is a flow diagram 800 provided to illustrate an exemplary process that may be performed in order to create a 2D synthesized image using the plurality of object maps created through the hierarchical multi-level feature image synthesizer in accordance with one embodiment of the disclosed inventions. At step 802, an image data set is acquired. The image data set may be acquired by a tomosynthesis acquisition system, a combination tomosynthesis/mammography system, or by retrieving pre-existing image data from a storage device, whether locally or remotely located relative to an image display device. At step 804, for each 2D image slice (e.g., Tr image slice), filters associated with the various hierarchical multi-level features (e.g., a high-level feature module, a mid-level feature module and a low-level feature module) corresponding to a particular 3D object are applied.

For example, filters associated with the high-level feature module, mid-level feature module and low-level feature module may be applied to each image of the Tr stack. At step 806, feature maps are generated by each hierarchical multi-level feature module (e.g., 3 feature maps are outputted assuming there are three multi-level feature modules associated with a particular 3D object. At step 808, the feature maps generated by the high-level feature module, mid-level feature module and the low-level feature module are combined to form an object map by using a learning library. The learning library utilizes the generated feature maps to determine a probability that the particular 3D object is located at a particular location of the Tr image slice. At step 810, multiple object maps corresponding to multiple Tr image slices are stacked to create a 3D breast volume. At step 812, a synthesized 2D image is created using the plurality of object maps in the 3D breast volume. At step 814, the synthesized 2D image is displayed to the end-user.

Having described exemplary embodiments, it can be appreciated that the examples described above and depicted in the accompanying figures are only illustrative, and that other embodiments and examples also are encompassed within the scope of the appended claims. For example, while the flow diagrams provided in the accompanying figures are illustrative of exemplary steps; the overall image merge process may be achieved in a variety of manners using other data merge methods known in the art. The system block diagrams are similarly representative only, illustrating functional delineations that are not to be viewed as limiting requirements of the disclosed inventions. It will also be apparent to those skilled in the art that various changes and modifications may be made to the depicted and/or described embodiments (e.g., the dimensions of various parts), without departing from the scope of the disclosed inventions, which is to be defined only by the following claims and their equivalents. The specification and drawings are, accordingly, to be regarded in an illustrative rather than restrictive sense.

What is claimed is:

1. A method for processing breast tissue image data, comprising: processing image data of a patient's breast tissue to generate a set of image slices that collectively depict the patient's breast tissue;
   applying one or more filters associated with a plurality of multi-level feature modules to each image slice of the set, wherein the multi-level feature modules are configured to recognize at least one assigned feature of a high-dimensional object that may be present in the patient's breast tissue;
   at each multi-level feature module of the plurality, generating a feature map depicting regions in the respective image slice having the at least one assigned feature; and
   combining the generated feature maps into an object map that indicates a probable location of the respective high-dimensional object, wherein the at least one feature of the high-dimensional object includes at least one of a low-level feature, a mid-level feature, and a high-level feature.

2. The method of claim 1, further comprising creating a two-dimensional synthesized image of the patient's breast tissue, including identifying one or more high-dimensional objects based at least in part on object maps generated for a plurality of the image slices.

3. The method of claim 1, wherein a learning library-based combiner is used to combine the generated feature maps into object maps.

4. The method of claim 1, wherein a voting-based combiner is used to combine the generated feature maps into object maps.

5. The method of claim 1, wherein the multi-level feature modules are configured to represent the respective at least one assigned feature of a high-dimensional image object.

6. The method of claim 5, wherein the high-dimensional image object is defined to represent a specific breast lesion or a type of breast structure.

7. The method of claim 5, wherein the high-dimensional image object comprises a three-dimensional image object.

8. The method of claim 1, wherein the at least one feature of the high-dimensional object is the low-level feature, and wherein the low-level feature is based upon a general image filter selected from a group comprising an edge filter, a line filter, and a gradient filter.

9. The method of claim 1, wherein the at least one feature of the high-dimensional object is the mid-level feature, and wherein the mid-level feature is based upon an algorithm or algorithmic model that represents and recognizes at least one of simple geometric shapes and image patterns.

10. The method of claim 9, wherein the at least one of simple geometric shapes and image patterns comprise circular shapes, lobulated shapes and dense objects.

11. The method of claim 1, wherein the at least one feature of the high-dimensional object is the high-level feature, and wherein the high-level feature is based upon an algorithm or algorithmic model that represents and recognizes at least one of complex geometric shapes and image patterns.

12. The method of claim 11, wherein the at least one of complex geometric shapes and image patterns comprise types of breast lesions and breast structures.

13. The method of claim 1, further comprising decomposing and representing the respective high-dimensional image object by a plurality of multi-level features designed to represent specific characteristics of the high-dimensional image object.

14. The method of claim 1, further comprising generating a three-dimensional volumetric object map based upon respective object maps created for of a plurality of image slices.

15. The method of claim 14, further comprising abstracting the three-dimensional volumetric object map to generate a three-dimensional volumetric object grid comprising a set of abstract three-dimensional image objects having differing attributes.

16. The method of claim 14, wherein the three-dimensional volumetric object grid comprises object probability values for individual grid voxels, and wherein the differing attributes include one or more of location, size, and shape.

17. The method of claim 1, wherein the object maps derived from a plurality of image slices are used to determine one or more of a location, size, shape, and morphology of the high-dimensional object.

* * * * *